US008835508B2

(12) United States Patent
    Zhou

(10) Patent No.: US 8,835,508 B2
(45) Date of Patent: Sep. 16, 2014

(54) STABLE AQUEOUS SOLUTION CONTAINING SODIUM PYRUVATE, AND THE PREPARATION AND USE THEREOF

(76) Inventor: Fangqiang Zhou, Forest Park, IL (US)

( * ) Notice: Subject to any disclaimer, the term of this patent is extended or adjusted under 35 U.S.C. 154(b) by 646 days.

(21) Appl. No.: 12/425,748

(22) Filed: Apr. 17, 2009

(65) Prior Publication Data

US 2009/0232908 A1    Sep. 17, 2009

Related U.S. Application Data

(63) Continuation of application No. PCT/CN2007/070918, filed on Oct. 18, 2007.

(30) Foreign Application Priority Data

Oct. 18, 2006   (CN) .......................... 2006 1 0117237

(51) Int. Cl.
    *A61K 33/14*   (2006.01)
    *A61K 31/22*   (2006.01)
    *A61K 9/08*    (2006.01)
    *A61K 31/19*   (2006.01)
    *A61K 9/00*    (2006.01)
    *A61K 47/02*   (2006.01)

(52) U.S. Cl.
    CPC . *A61K 31/19* (2013.01); *A61K 9/08* (2013.01); *A61K 9/0019* (2013.01); *A61K 31/22* (2013.01); *A61K 47/02* (2013.01)
    USPC .......................... 514/675; 424/677; 514/546

(58) Field of Classification Search
    USPC .............................. 424/601; 514/25
    See application file for complete search history.

(56) References Cited

U.S. PATENT DOCUMENTS

| 4,649,050 | A | * | 3/1987 | Veech | 424/601 |
| 5,443,848 | A |   | 8/1995 | Kramer et al. | |
| 6,307,080 | B1 | * | 10/2001 | Pischel et al. | 556/131 |
| 6,492,336 | B1 | * | 12/2002 | Mahiout | 514/25 |
| 6,846,842 | B2 |   | 1/2005 | Ajami et al. | |
| 2005/0058724 | A1 |   | 3/2005 | Veech | |

FOREIGN PATENT DOCUMENTS

| CN | 1559391 A | | 1/2005 | | |
| DE | 0658353 | * | 11/1993 | .............. | A61M 1/34 |
| JP | 60-78936 | * | 5/1985 | .............. | C07C 59/19 |
| JP | 4-47656 B2 | | 8/1992 | | |
| JP | 4047656 B2 | | 11/2007 | | |
| WO | 2005/084635 A2 | | 9/2005 | | |

OTHER PUBLICATIONS

Office Action issued Apr. 3, 2009 by the State Intellectual Property Office of China in related application No. CN 200610117237.3.
International Search Report of PCT/CN2007/070918, dated Jan. 24, 2008.
Mongan et al. "Pyruvate improves cerebral metabolism during hemorrhagic shock." Am J Physiol Heart Physiol, vol. 281, Aug. 2001, 99. H854-H864.
Hermann et al. "Haemodynamic effects of intracoronary pyruvate in patients with congestive heart failure: an open study." The Lancet, vol. 535, Apr. 17, 1999, pp. 1321-1323.
Yi et al. "Systemic pyruvate administration markedly reduces infarcts and motor deficits in rat models of transient and permanent focal cerebral ischemia." Neurobiology of Disease, vol. 26, 2007, pp. 94-104.
Zhou "Pyruvate in the Correction of Intracellular Acidosis: A Metabolic Basis as a Novel Superior Buffer." Am J Nephrol, 25, 2005, pp. 55-63.
Kraut et al. "Use of Base in the Treatment of Severe Acidemic States." American Journal of Kidney Diseases, vol. 38 (4), Oct. 2001, pp. 703-727.
Stanley et al. "Post-Ischemic Treatment with Dipyruvyl-Acetyl-Glycerol Decreases Myocardial Infarct Size in the Pig." Cardiovascular Drugs and Therapy, 17, 2003, pp. 209-216.
Sims et al. "Ringer's ethyl pyruvate solution ameliorates ischemia/reperfusion-induced intestinal mucosal in rats." Crit Care Med, vol. 29 (8), 2001, pp. 1513-1518.
Venkataraman et al. "Resuscitation with Ringer's Ethyl Pyruvate Solution Prolongs Survival and Modulates Plasma Cytokine and Nitrite/Nitrate Concentrations in a Rat Model of Lipopolysaccharide-Induced Shock." SHOCK, vol. 18(6), 2002, pp. 507-512.
Mallet et al. "Metabolic Cardioprotection by Pyruvate: Recent Progress." Exp Biol Med (Maywood), 230, 2005, pp. 435-443.
Wang et al. "Effects of pyruvate buffered peritoneal dialysis solution on peritoneal microphages function, electrolytes metabolism, acid-base balance and peritoneal mesothelium in uremic rats." Chin J Nephrol, vol. 17(6), 2001, pp. 365-368.
Mongan et al. "Intravenous pyruvate prolongs survival during hemorrhagic shock in swine." Am. J. Physiol 227 (Heart Circ Physiol 46), 1999, pp. H2253-H2263.
Nascimento Jr. et al. "Hypertonic 15% Sodium Pyruvate Offers No Initial Resucitation Advantage Compared with 8% Hypertonic NaC1 in Sheep with Multiple Hemorrhages." SHOCK, vol. 27(5), 2007, pp. 565-571.
Andrae et al. "Pyruvate and Related α-Ketoacids Protect Mammalian Cells in Culture Against Hydrogen Peroxide induced Cytotoxicity." Toxicology Letters, 28, 1985, pp. 93-98.
Slovin et al. "Sodium pyruvate is better than sodium chloride as a resuscitation solution in a rodent model of profound hemorrhagic shock." Rescucitation, 50, 2001, pp. 109-115.
Zhou. "Advantages of pyruvate over lactate in peritoneal dialysis solutions." Acta Pharmacol Sin, vol. 22(5), May 2001, pp. 385-392.
Wu et al. "Pyruvate Improves Neutrophilic Nitric Oxide Generation in Peritoneal Dialysis Soultion." Artificial Organs, vol. 29(12), 2005, pp. 976-980.
Margolis et al. "Identification and Quantitation of the Impurities in Sodium Pyruvate." Anal Chem, vol. 58 (12), Oct. 1986, pp. 2504-2510.

(Continued)

*Primary Examiner* — Walter Webb
(74) *Attorney, Agent, or Firm* — Hamre, Schumann, Mueller & Larson, P.C.

(57) ABSTRACT

A stable aqueous solution of sodium pyruvate for medical use, which contains 10-1,200 mM sodium pyruvate and a stabilizer of sodium pyruvate, wherein the said stabilizer is $H^+$ which leads to pH 3.0-6.0 or NaCl which provides at least 20 mM $Na^+$.

10 Claims, No Drawings

(56) References Cited

OTHER PUBLICATIONS

Doucet et al. "Limited Resuscitation with Hypertonic Saline, Hypertonic Sodium Acetate, and Lactated Ringer's Solutions in a Model of Uncontrolled Hemorrhage from a Vascular Injury." The Journal of Trauma: Injury, Infection, and Critical Care, vol. 47 (5), 1999, pp. 956-963.

* cited by examiner

STABLE AQUEOUS SOLUTION CONTAINING SODIUM PYRUVATE, AND THE PREPARATION AND USE THEREOF

PRIORITY INFORMATION

This application is being filed as a Continuation of PCT International Application Number PCT/CN2007/070918 entitled STABLE AQUEOUS SOLUTION CONTAINING SODIUM PYRUVATE, AND THE PREPARATION AND USE THEREOF of which the International Filing date is Oct. 18, 2007 which claims the benefit of priority of CN 200610117237.3, filed Oct. 18, 2006, both of which are hereby incorporated by reference in their entirety.

FIELD OF THE INVENTION

The invention refers to the field of medicine, particularly to the aqueous solution of sodium pyruvate for medical use.

BACKGROUND

Pyruvate (Pyr) is a normal component in the body of human, animals and plants. It is a product of glycolysis, which is a biological basic metabolism. It is at the convergence of metabolisms of sugar, fat and protein and it is a critical starting substance for Tricarboxylic Acid Cycle (TCA cycle). In recent decades, large numbers of in vitro and in vivo animal experiments and a few clinical trials strongly showed that sodium pyruvate (Sod Pyruvate, NaPyr) can substantially protect functions of multiple cell lines and organs, particularly ischemia-reperfusion injury of some important organs, such as heart, liver, brain and kidney, without toxic side effects (Am J Physical 281:H854-64, 2001; Lancet 353:1321-3, 1999; Neurobiol Dis 26:94-104, 2007).

Otherwise, recent studies suggested that NaPyr would be a superior buffer for correcting severe metabolic acidosis. The severe metabolic acidosis is severe clinical conditions, such as type A (anoxic type) lactic acidosis, diabetic ketoacidosis and hypercapnia with cardiac arrest, which comprise more than 90% of severe metabolic acidosis (pHa $\leq 7.10$). Heretofore, no ideal buffer has been used in the art worldwide. Numerous in vitro and in vivo animal experiments demonstrated that NaPyr has special effects on improving intracellular and extracellular acidosis. Noticeably, NaPyr could exert important effects even under anoxic conditions, which is particularly suitable for the above mentioned severe acidosis. More importantly, NaPyr is not only a buffer, it also has direct therapeutic effects on dysfunction of primary affected organs causing the above mentioned severe conditions. It makes NaPyr completely different from sodium lactate, which has been used for more than half a century, and sodium bicarbonate, which has been used longer. Both sodium lactate and sodium bicarbonate are not suitable for the above mentioned severe acidosis, and they have toxicity (Am J Nephrol 25:55-63, 2005; Am J Kidney Dis 38:703-27, 2001).

Clinically, Pyr seems to be a potential effective medicine, especially in the field of intensive care and dialysis. However, an extensively accepted conception is that aqueous solution containing pyruvate or sodium pyruvate is very unstable at room temperature, because the chemical property of keto is unstable, which can produce dimer (4-hydroxy-4-methyl-2-ketoglutaric acid, also known as parapyruvate) and other polymeric derivatives by spontaneous aldol-like condensation and a small amount of hydrates by hydration in non-enzyme catalysis. The polymer is cytotoxic, and is an inhibitor of the enzyme in TCA cycle in mitochondria and lactate dehydrogenase (LDH). The hydrate makes Pyr lose its metabolic activity. The conclusion made 20 years ago by the authoritative report of NBS: Center for Analysis Chemistry, National Bureau of Standards, USA was that aqueous solution containing NaPyr is unstable at 22° C., pH >6.0, as determined by High Performance Liquid Chromatography (HPLC) and Nuclear Magnetic Resonance (NMR). At room temperature and pH 7.3, the content of dimer can reach 9.1% in high concentration 3.0 M (3,000 mM) of pure NaPyr in water after 24 hours, and can reach 18.4% after 48 hours (Anal Chem 58:2504-10, 1986). It is commonly considered that the perfusion solution containing NaPyr should be prepared freshly and be used as soon as possible. It was indicated in US patent 20050058724 that the aqueous solution containing pyruvate anion could not be used as therapeutic fluids for human. Some studies indicated that under low temperature (4-8° C.), 0.1M HCl or 0.1 M NaCl could make aqueous solution containing NaPyr stable. The effect of various concentrations of HCl or NaCl on the stability of NaPyr under room temperature or high temperature (e.g. 40° C.) was not shown. Room temperature or high temperature is a common condition for clinical usage, manufacturing or storage. Therefore, no pharmaceutical company could produce aqueous solution containing stable Pyr at room temperature in the world, including intravenous injection solution and dialysis solution. Except for some clinical trials, aqueous solution containing NaPyr has never been used in routine clinical practice.

In order to solve the above problem and deliver a large amount of Pyr into the body to achieve the aim of treatment, the direction of R&D in recent years (i.e. since the brief report originally published on Surgical Forum in 1999) is to develop ester derivatives of Pyr, such as Ethyl Pyruvate (EP), which is Ringer's solution with NaLac replaced by EP (Ringer's Ethyl Pyruvate Solution, REPS) and Dipyruvyl Acetyl Glycerol (DPAG). Some in vivo experiments showed their inspiring therapeutic effects (Minerva Anestesiol 67:190-2, 2001, Cardiovasc Drugs Ther 17:209-16, 2003), and they were also filed for patent protection, as described in U.S. Pat. No. 6,846,842. However, the developments in these aspects also hold back further investigation of the stability of aqueous solution containing NaPyr. The ester derivatives of Pyr still have the following disadvantages although the research of EP is in full swing: 1, EP can be solved and stabilized only by binding with calcium ion, and it should be solved in Ringer's equilibrium solution which contains calcium chloride (2.7 mEq/L) to be used in laboratories (Crit Care Med 29:1513-8, 2001), and its concentration is only 28 mM and could not be prepared as isotonic and hypertonic solution purely containing EP. 2, Ester cannot be ionized as $Pyr^-$ in water, but can be spontaneously hydrolyze as $Pyr^-$ through esterase or non-enzyme pathway (thereby producing hydrogen ion [$H^+$]). In contrast to NaPyr, esters of Pyr are not buffer and can produce the same amount of [$H^+$] through in vivo hydrolysis. In vivo tests of shocked animal showed that although shock was improved with REPS, EP, per se, could not correct acidosis (Shock 18:507-12, 2002) and EP could not be prepared as a buffer used in dialysis solution, either. 3, The concentration of chloride ion in REPS was still so high that transfusion of a large volume of REPS would lead to hyperchloremic acidosis. 4, On the market, as a raw material, the esters of Pyr are not as plentiful as sodium salt of Pyr. Thus, the esters of Pyr cannot replace aqueous solution containing NaPyr mostly in clinical practice.

Therefore, there is an urgent need in the art to provide a stable aqueous solution containing Pyr, which can deliver the Pyr with superior features into the body effectively, i.e.

improve metabolic pathways in vivo, together with protecting vital organs' functions and improving metabolic disorders.

SUMMARY OF THE INVENTION

The invention provides a stable aqueous solution containing Pyr.

The invention provides a method for preparation of the above mentioned aqueous solution.

The invention provides the use of the above mentioned aqueous solution.

In first aspect of the invention, it provides an aqueous solution containing sodium pyruvate for medical use. The solution contains the following components:
(a) 10-1200 mM sodium pyruvate;
(b) a stabilizer of sodium pyruvate, which is selected from:
   (b1) hydrogen ion, which makes the solution at pH of 3.0-6.0; and/or
   (b2) NaCl, which provides additional $Na^+$ of at least 20 mM;
(c) pharmaceutically accepted water for solvents, and after the solution is stood for 6 months under 25° C., the content of sodium pyruvate in the solution satisfies the following equation:

$$\frac{C_{the\ sixth\ month}}{C_{zero\ time}} \times 100\% \geq 95\%$$

wherein, $C_{the\ sixth\ month}$ means the concentration of sodium pyruvate in the solution after 6 months, $C_{zero\ time}$ means the initial concentration of sodium pyruvate in the solution of zero time.

In another preferred embodiment, after the solution is stood for 6 months under 25° C., the content of sodium pyruvate in the solution satisfies the following equation:

$$\frac{C_{the\ sixth\ month}}{C_{zero\ time}} \times 100\% \geq 98\%$$

wherein, $C_{the\ sixth\ month}$ means the concentration of sodium pyruvate in the solution after 6 months, $C_{zero\ time}$ means the initial concentration of sodium pyruvate in the solution of zero time.

In another preferred embodiment, the molar ratio between the dimer of sodium pyruvate in the solution after being stood under 25° C. for 6 months and sodium pyruvate of zero time is less than 1:20 (<5%).

In another preferred embodiment, the molar ratio between the dimer of sodium pyruvate in the solution after being stood under 25° C. for 6 months and sodium pyruvate of zero time is less than 1:50 (<2%).

In another preferred embodiment, the aqueous solution containing sodium pyruvate for medical use contains 10-1,200 mM sodium pyruvate, preferably 100-1,000 mM, most preferably 300-1,000 mM.

In another preferred embodiment, the aqueous solution containing sodium pyruvate for medical use is at pH of 3.5-5.5, preferably 4.0-5.0, most preferably 4.5±0.1.

In another preferred embodiment, the aqueous solution containing sodium pyruvate for medical use contains 1,000 mM sodium pyruvate.

In another preferred embodiment, the aqueous solution for medical use is a hyperosmotic solution which contains 100-1,000 mM sodium pyruvate and 200-800 mM NaCl at pH 4-6, and the osmotic pressure of which is 2,000-3,000 mOsm/L.

In another preferred embodiment, the aqueous solution for medical use is a compound normal saline containing 80-20 mM sodium pyruvate and 80-130 mM NaCl.

In another preferred embodiment, the aqueous solution for medical use contains 10-80 mM $Pyr^-$, 120-150 mM $Na^+$, 90-130 mM $Cl^-$, 1-4 mM $K^+$, 1-5.0 mM $Ca^{2+}$, and 0.1-11.0 mM $Mg^{2+}$.

In another preferred embodiment, the aqueous solution for medical use further contains 1-10% hydroxyethyl starch or 1-10% dextran.

In another preferred embodiment, the above mentioned hydroxyethyl starch is Hydroxyl Starch 200/0.5 or Hydroxyl Starch 130/0.4.

In another preferred embodiment, the above mentioned dextran is dextran-70.

In the second respect of the invention, it provides a method for preparation of the above mentioned aqueous solution for medical use, which comprises the steps of:

Mixing sodium pyruvate, a stabilizer of sodium pyruvate and pharmaceutically accepted water for solvents to form the above mentioned aqueous solution for medical use, wherein the solution for medical use contains (a) 10-1,200 mM sodium pyruvate, (b) a stabilizer of sodium pyruvate, which is selected from:
   (b1) hydrogen ion, which makes the solution at pH of 3.0-6.0; and/or
   (b2) NaCl, which provides additional $Na^+$ of at least 20 mM.

In another preferred embodiment, the method comprises the steps of:

Mixing pure sodium pyruvate powder, a stabilizer of sodium pyruvate and pharmaceutically accepted water for solvents (containing pure water for injection, NaCl solution in different concentrations and electrolyte equilibrium solution) to form the above mentioned aqueous solution for medical use, wherein the aqueous solution for medical use contains (a) 10-1,200 mM sodium pyruvate, (b) a stabilizer of sodium pyruvate, which is selected from:
   (b1) hydrogen ion, which makes the solution at pH of 3.0-6.0; and/or
   (b2) NaCl, which provides additional $Na^+$ of at least 20 mM.

In another preferred embodiment, the mixing step comprises:
a. dissolving sodium pyruvate in water for medical injection to form 10-1,200 mM sodium pyruvate solution;
b. adding $Na^+$ of not less than 20 mM or electrolyte of different concentrations (selected from but not limited to calcium chloride, magnesium chloride and potassium chloride) or adjusting to pH 3.0-6.0 with HCl, to obtain the above mentioned aqueous solution for medical use.

In another preferred embodiment, the method also comprises the step of: further adding optional colloidal additives or glucose. The mentioned colloidal additives include hydroxyethyl starch or dextran.

In the third respect of the invention, it provides a kit which comprises:
(i) container 1, which contains solution 1, and said solution 1 is the above mentioned aqueous solution for medical use, and
(ii) container 2, which contains solution 2, and said solution 2 is mixed with solution 1 before use.

In another preferred embodiment, the invention provides a double-chambered bag, which comprises:

(i) container 1, which contains solution 1, and said solution 1 is the above mentioned aqueous solution for medical use, and (ii) container 2, which contains solution 2, and said solution 2 is mixed with solution 1 before use.

In another preferred embodiment, the solution 2 in the said kit is selected from the group consisting of: 100-800 mM NaCl solution, and/or 0-25 mM sodium lactate, and 1.0-110.0% glucose or colloidal additives after mixing with solution 1.

In another preferred embodiment, the solution 2 in the said kit comprises electrolytes of different concentrations. The said electrolyte selected from but not limited to calcium chloride, magnesium chloride and potassium chloride. The said colloidal additives include hydroxyethyl starch or dextran.

In another preferred embodiment, the solution 1 in the said kit comprises 10-800 mM sodium pyruvate, pH 4.0-5.0.

In another preferred embodiment, the solution 1 in the said kit comprises 250-400 mM sodium pyruvate, pH 4.5±0.1.

In the forth respect of the invention, it provides the use of the above mentioned aqueous solution for medical use in preparation of shock-resuscitation solution, intravenous therapeutic solution, organ protection solution, metabolic correction solution, dialysis fluid, hemofiltration substitute solution, cell rejuvenation solution, cardioplegia solution and extracorporeal circulation machine priming solution (used in open heart-lung surgery), etc.

In another preferred embodiment, the said organs that present dysfunctions and disorders include heart, liver, kidney and brain, etc.

In another preferred embodiment, the said metabolic disorders include severe hypoglycemia, severe metabolic acidosis, etc. The said metabolic acidosis includes hyperlactatemia and lactic acidosis, diabetic and alcoholic ketoacidosis and hypercapnia associated with circulatory arrest.

In another preferred embodiment, the said dialysis fluid includes peritoneal dialysis solution, hemofiltration substitute solution and hemodialysis solution.

In another preferred embodiment, the said peritoneal dialysis solution is used in peritoneal dialysis treatment for patients suffered from renal failure.

In another preferred embodiment, the said hemofiltration substitute solution is applied in hemofiltration therapy for patients suffered from renal failure and severe metabolic acidosis and disorder of lactate metabolism.

Thereby, the invention provides a stable aqueous solution of NaPyr, which can deliver the Pyr with superior features into the body effectively, i.e. improve metabolic pathways in vivo, together with the protection of vital organs' functions and the improvement of metabolic disorders.

DETAILED DESCRIPTION OF THE INVENTION

Through extensive and intensive study, the inventor unexpectedly discovered that although the aqueous solution containing 3.0-4.5 M (close to saturation) NaPyr is quite unstable, the aqueous solution containing low to medium concentrations (10-1,200 mM) of NaPyr and some stabilizers of sodium pyruvate is stable under room temperature. Hereby, the aqueous solution of sodium pyruvate for medical use was prepared for the first time. In particular, the said stabilizer of sodium pyruvate is hydrogen ion, which makes the solution at pH of 3.0-6.0; and/or the said stabilizer of sodium pyruvate is NaCl, which provides additional $Na^+$ of at least 20 mM.

Meanwhile, various formulations, such as various kinds of solutions used for shock-resuscitation and intravenous fluid therapy, solutions for protecting the important organs (heart, liver, kidney, brain, etc.) from dysfunction and correcting severe metabolic acidosis, and the peritoneal dialysis fluid for replacement therapy of renal failure or hemofiltration substitute solution, artificial heart-lung machine priming solution or hemocyte rejuvenation solution, and the like were produced accordingly.

In order to illustrate the invention, the main mechanisms about cell protection of NaPyr are described herein (Toxicol Lett 28:93-8, 1985; Am J Nephrol 25:55-63, 2005; Exp Biol Med (Maywood) 230:435-43, 2005). But it should not be understood to limit the invention.

Firstly, the pathways of cell protection of NaPyr relate to various aspects:

1, it is a strong anti-oxidant. Pyr can be a scavenger of oxidants in vivo by forming $H_2O$ and $CO_2$ (and acetic acid) through quick oxidative decarboxylation reaction with the oxidant ($H_2O_2$ and oxygen free radical: $OH^-$, $O_2^-$) under non-enzyme condition. It also can clear nitrogen free radical (NO, $ONOO^-$) effectively. In vitro assay shows that normal plasma concentration of Pyr has a substantial anti-oxidative effect.

2, it can improve intracellular redox potential (enhance reduction capacity: increasing $NAD^+$/NADH directly and raising the ratio of GSH/GSSG indirectly).

3, it can protect glycolysis under hypoxic condition, delay the decline of ATP produced by glycolysis, and retain the basic cellular function, such as the integrity of cell membrane and ion channel, which functions only in the presence of glycolytically derived ATP.

4, it can stimulate oxidative metabolism of TCA cycle through the enhancement of pyruvate dehydrogenase complex (PDC) activity by inhibiting pyruvate dehydrogenase kinase (PDH kinase). It can also promote aerobic oxidation of TCA cycle by enhancing anaplerosis and increasing the concentration of pyruvate as the substrate.

5, it can correct intracellular acidosis efficiently. In addition to its low buffer coefficient, it can consume intracellular hydrogen ion to increase pH value under anoxic condition (being reduced to lactic acid by lactate dehydrogenase, LDH), thereby consuming an intracellular $[H^+]$: pyruvate $+2$-$[H] \rightarrow$ lactate, wherein one negative hydrogen ion $[H^-]$ is from coupled oxidizing reaction: $NADH \rightarrow NAD^+ + [H^-]$ and another $[H^+]$ is from cytoplasma $2[H]=1[H^+]+1[H^-]$, which are used by Pyr, the former is from cytoplasma and the latter is from NADH. Consuming one $[H^+]$ in cytoplasma is equivalent to reserving one $HCO_3^-$, which can increase the content of $HCO_3^-$ and pH value in the blood) or aerobic oxidation (also consuming one $[H^+]$ during oxidative phosphorylation of TCA cycle). The hydrogen consumption of Pyr-based gluconeogenesis is one fold more than that of lactate-based gluconeogenesis (Lac: $H^+=1:1$; Pyr:$H^+=1:2$).

6, it can inhibit the activation of inflammatory mediators: PKC, NF-kB, TNF-alpha, etc; maintain equilibrium of intracellular calcium ion and prevent apoptosis, and others. Otherwise, it can improve anoxia blood rheological abnormality and is helpful to advance oxygen supplying for tissues and organs.

Secondly, the functions of NaPyr are widespread:

1, As pyruvate is a metabolite of glucose metabolism and at the convergence of metabolisms of three major nutrients, it has extensive effects on metabolism in vivo.

2, As the basic redox reaction via LDH (even under anaerobic state) or oxidative phosphorylation of TCA cycle (under aerobic state) exists widely in mammalian cells and various tissues and organs of human body, it can exert protective effects on various important organs under both anoxic and aerobic conditions.

3, Further, because the whole blood concentration of pyruvate is extremely low in normal human body, which is only 0.3-0.9 mg % (0.03-0.08 mM, even lower in kidney cells, suggesting it is highly metabolically active), and the therapeutic dosage of pyruvate (2-10 mM) can reach tens to hundreds fold of its blood concentration.

The above mentioned mechanisms thoroughly illustrate the basis of prevalent and effective applications of NaPyr.

Chemically, sodium pyruvate is unchanging by autoclaving. An In vivo animal experiment in peritoneal dialysis demonstrated that the aqueous solution containing sodium pyruvate was stable during the process of regular autoclaving sterilization, and its therapeutic effect was still better than that of the control also treated by autoclave treatment, and no toxicity was observed (Chin J Nephrol 17: 365-8, 2001).

1. Aqueous Solution of Pure Sodium Pyruvate:

The invention provides aqueous solution of pure sodium pyruvate containing 20-1,200 mM, preferably 50-800 mM, most preferably 100-700 mM sodium pyruvate, at pH 4.0-5.0. The preferred pH is 4.5.

The aqueous solution of pure NaPyr provided by the invention can be used to treat dysfunctions of organs, including heart, liver, kidney and brain, etc., or metabolic disorders, such as severe hypoglycemia, and severe acidosis, etc.

Preferably, the invention provides 250-500 ml of 11.0M (11.0%) NaPyr at pH 4.5 to be applied in the treatment of severe diseases and severe metabolic acidosis.

The aqueous solution of pure sodium pyruvate provided by the invention can be administered to treat diabetic ketoacidosis combined with intravenous insulin: to recover (or increase) the sensitivity of insulin receptors inhibited by acidosis, decreasing the dosage of insulin, and accelerating the oxidation of ketone bodies. The aqueous solution of sodium pyruvate provided by the invention can be employed to prevent and cure severe hypoglycemia complications. The aqueous solution of pure sodium pyruvate at pH 4.5 provided by the invention can also be packed in a specialized combination, to be intravenously instilled using a double-chambered bag. The aqueous solution of pure sodium pyruvate can be mixed, before use, with another bag of solution, such as weak alkaline aqueous solution, glucose solution or electrolyte solution and/or colloidal solution, to form the following solutions.

2. Hyperosmotic Aqueous Solution of NaCl/NaPyr:

The invention provides hyperosmotic aqueous solution of NaCl/NaPyr, which contains 100-1,000 mM NaPyr and an equal or higher molar concentration of NaCl, at pH 4-6. Preferably, the hyperosmotic aqueous solution of NaCl/NaPyr contains 300-800 mM NaPyr and an equal or higher molar concentration of NaCl. More preferably, the hyperosmotic aqueous solution of NaCl/NaPyr contains 650 mM (7.15%) NaPyr and 650 mM (3.8%) NaCl, with 2,600 mOsm/L in total.

1-10%, preferably 6% Hydroxyethyl Starch can be added into the hyperosmotic aqueous solution of NaCl/NaPyr. The preferred Hydroxyethyl Starch is Hydroxyethyl Starch 200/0.5 or Hydroxyethyl Starch 130/0.4.

Alternatively, 1-10%, preferably 6% Dextran can be added into the hyperosmotic aqueous solution of NaCl/NaPyr. The preferred Dextran is Dextran-70.

The invention also provides a combination with double-chambered bags, which comprises two solutions, wherein one contains pure sodium pyruvate (pH4.0-5.0), and another contains weak alkaline solution of NaCl. The two solutions should be mixed completely before injection to obtain a hyperosmotic solution of NaCl/NaPyr having a preferred osmotic pressure of 2,000-3,000 mOsm/L, pH 6-7.5. The ratio of NaCl and NaPyr can be various, but not limiting to 1:1.

The hyperosmotic aqueous solution of NaCl/NaPyr provided by the invention can be used in the treatment of shock induced by various etiologies, such as hemorrhage or sepsis. It can avoid toxicity of hyperchloremic acidosis triggered by hyperosmotic saline solutions used extensively in treating shock (such as 7.5% NaCl solution). Meanwhile, NaPyr exerts effects of organ protection and anti-acidosis, especially for tissue ischemia or hypoxia induced by shock.

The experiments indicated that pure hypertonic or isotonic NaPyr and NaCl having the equal osmotic pressure had the comparable therapeutic effect of anti-hemorrhagic shock. However, hyperchloremic acidosis, which deteriorates original acidosis was reported in NaCl group. Thus, hyperchloremia, which is induced by hypertonic saline solutions (such as 7.5% NaCl solution), makes shock complicated. On the other hand, neither hyperchloremic acidosis, nor lactic acidosis was reported in NaPyr group. Although blood lactate level of NaPyr group was increased, the ratio of blood lactate/Pyr was decreased (suggesting increase of ratio of intracellular $NAD^+/NADH$) and pH of arterial blood was increased, and the survival rate of animals was increased substantially (Am J Physiol 277:H2253-63, 1999; Am J Physiol 281:H854-64, 2001; Shock 27:565-71, 2007; Resuscitation 50:109-15, 2001).

Although it has not reported to date that hyperosmotic solution of NaCl/NaPyr (or containing hydroxyethyl starch) can be used in reducing intracranial hypertension induced by trauma and/or hypoxia, it will, theoretically, have the similar or better effect than the existing hyperosmotic NaCl solution and mannitol solution.

In vivo animal experiments showed the effectiveness of an experimental hypertonic compound sodium acetate (NaAc) solution of NaCl/NaAc (50%/50%): increasing blood pressure and pH of arterial blood (pHa) because of decline of introduced $Cl^-$, and acetate is a buffer correcting acidosis. But acetate has the effect of making cardiovascular system unstable, and 50% NaAc cannot improve acidosis of gastrointestinal tract mucosa (intracellular pH: pHi). Although pHa is increased, pHi is more critical in intensive care (J Trauma 47:956-63, 1994). An aqueous solution of NaCl/NaAc was published in U.S. Pat. No. 5,443,848. In the past two decades, it appeared a series of crystalloid and colloid dissolved with modified balance solutions containing low concentration of sodium acetate, such as PlasmaLyte A (Baxter, USA), Ringerfundin and Tetraspan (B. Braun, Germany), etc. However, acetate does not exert effects under anoxic conditions. The oxygen consumption of acetate is far more than that of pyruvate during aerobic metabolism. In addition, acetate is not of obvious multiple organs protection, especially heart, brain and intestine. Therefore, the solutions containing sodium acetate are not perfect.

Recently, another experimental hypertonic (15%) aqueous solution of pure NaPyr was compared with identical hypertonic saline (8% NS). The result showed that except for alkalosis, over-concentrated NaPyr (15%) did not perform exquisitely better than NS although both of them had the comparable property of hemodynamics improvement (Shock 27:565-71, 2007). Thus, these solutions are not suitable in clinical settings.

The solution of NaCl/NaPyr, with 6% Hydroxyethyl Starch or 6% Dextran-70 added can further retain and extend the effects on cardiovascular and brain hemodynamics.

3. Compound Normal Saline:

The invention provides compound normal saline which contains 80-130 mM NaCl and 80-20 mM NaPyr, preferably 94-114 mM NaCl and 60-40 mM NaPyr, more preferably, 104 mM NaCl and 50 mM NaPyr, at pH of 4-6, more preferably 4.5±0.5.

In another preferred embodiment, the compound normal saline contains 126 mM NaCl and 28 mM NaPyr, pH 4-6, more preferably, pH 4.5±0.5.

1-10%, preferably 3-7%, more preferably 5% glucose can be added into the above mentioned compound normal saline.

As compared to normal saline (NS, 0.9% NaCl) in conventional clinical use, the concentration of $Na^+$ of the compound normal saline provided by the invention is still 154 mM and that of $Cl^-$ is in a range of normal blood concentration. It can prevent from causing any iatrogenic hyperchloremia. The 50 mM NaPyr (the concentration is one fold higher than that of sodium lactate in Ringer's solution (28 mM)) is delivered concurrently, although its blood concentration is not high in a single dose, it can prevent the tendency of acidosis or is suitable for the patients having the tendency of acidosis, particularly for peri-operative patients who need one single dose of large dosage (2-4 L or above). The compound normal saline in 500-1,000 ml or more is required in a single dose for those patients who need repeated deliveries of the compound normal saline, such as chronic renal dialysis patients. If the said solution is used in a long regular manner, it will be possible to protect the organ function, especially the residual renal function.

Adding 6% Hydroxyethyl Starch or 6% Dextran-70 into the compound normal saline of NaCl/NaPyr in various ratio can further preserve and extend the effects on cardiovascular and brain hemodynamics.

4. Modified Electrolyte Solution of NaPyr:

The invention provides a modified electrolyte solution of NaPyr containing Pyr: 10-80 mM, $Na^+$: 120-150 mM, $Cl^-$: 90-130 mM, $K^+$: 1-4 mM, $Ca^{2+}$: 1-5 mM, and $Mg^{1+}$: 0.1-1.0 mM; preferably, $Pyr^-$: 40-50 mM, $Na^+$: 130-140 mM, $Cl^-$: 95-125 mM, $K^+$: 2-4 mM, $Ca^{2+}$: 2-5 mM, and $Mg^{2+}$: 0.3-0.5 mM; more preferably, $Pyr^-$: 28 mM, $Na^+$: 140 mM, $Cl^-$: 119 mM, $K^+$: 3.0 mM, $Ca^{2+}$: 3.0 mM, and $Mg^{2+}$: 0.3 mM. The solution is at pH 4-6, preferably pH 4-5.0, more preferably pH 4.5.

The modified electrolyte solution of NaPyr provided by the invention is suitable for large volume resuscitation (2-4 L and above) for metabolic acidosis, particularly hyperlactacidemia and lactic acidosis.

6% Hydroxyethyl Starch or 6% Dextran-70 can be added to the modified electrolyte solution of NaPyr to further preserve and extend the effects on cardiovascular and brain hemodynamics.

Within the past ten years, some clinical trials apparently suggested that lactate Ringer's solution containing Hydroxyethyl Starch (the modified lactate electrolyte solution containing 6% Hydroxyethyl Starch and glucose, Hextend, BioTime, Inc. CA, USA) had better effects in major surgery with large volume resuscitation than that of lactate Ringer's solution and NS.

Although it can reduce incidence of hyperchloremic acidosis induced by bulky NS, Hextend, which contains 28 mM sodium lactate, and lactate Ringer's solution are not suitable for patients with hyperlactacidemia and lactic acidosis, which are often present in critical care patients with disorders of lactate oxidative metabolism. The modified electrolyte solution of NaPyr provided by the invention does or does not contain 1-10% Hydroxyethyl Starch or Dextran, with 28 mM NaLac replaced by 28 mM NaPyr (or 40-50 mM or more, NaCl is reduced accordingly by 12-22 mM), thereby, a new modified Ringer's injection solution of pyruvate with or without Hydroxyethyl Starch or Dextran is produced, which does not contain glucose (other electrolytes are also adjusted slightly). Accordingly, it can also be used for diabetic patients (when without Dextran).

Pyr in the modified electrolyte solution of NaPyr provided by the invention is stable in the aqueous solution and is effective for prevention and treatment of acidosis, which is better than lactate, especially when acidosis is induced with tissue ischemia and/or hypoxia.

The modified solution of 28 mM Pyr is suitable for the patients without metabolic acidosis. The modified solution containing 40-50 mM Pyr is suitable for the patients with metabolic acidosis, especially for those with hyperlactacidemia and lactic acidosis.

The modified electrolyte solution of NaPyr provided by the invention has therapeutic protective effects on acidosis and multi-organs injury caused by ischemia and/or hypoxia. Because a large dosage of Pyr (80-200 mM and above) is introduced during a large volume (2-4 L and above) of fluid treatment, and it is also suitable for hyperlactacidemia and lactic acidosis as compared to Hextend.

The modified electrolyte solution of NaPyr with or without Hydroxyethyl Starch provided by the invention is an effective replacement of plasma volume expander.

The ingredients and their concentrations (mM) in the above solutions are listed below:

|  | Hydroxyethyl Starch | $Lac^-$ | $Pyr^-$ | $Na^+$ | $Cl^-$ | $K^+$ | $Ca^{2+}$ | $Mg^{2+}$ | glucose |
|---|---|---|---|---|---|---|---|---|---|
| Lactate Ringer's solution |  | 28 |  | 130 | 109 | 4.0 | 1.35 |  |  |
| Hextend | 60 g | 28 |  | 143 | 124 | 3.0 | 5.0 | 0.9 | 0.99 g |
| Pyruvate Ringer's solution | (60 g) |  | 28 | 140 | 119 | 3.0 | 3.0 | 0.3 |  |
| Solution of the invention |  |  | 20-50 | 130-150 | 95-125 | 1-4 | 2-5 | 0.1-0.5 |  |

5. Dialysis Solution Containing Pyruvate:

It is well known that in Lactate-based Peritoneal Dialysis Solution (L-PDS), high concentration of glucose, lactate and acidic pH (one or the combination thereof) are toxic to peritoneal cavity and general metabolism (bioincompatibility).

When the lactate or bicarbonate in PDS is replaced by Pyr, the biocompatibility of PDS can be improved. Because the capacity of correcting acidosis of Pyr is better than that of lactate and bicarbonate under the identical molar concentration (40 mM), and Pyr has no toxicity. Therapeutic large dosage of Pyr has the cell/organ protective effect when it passes through peritoneal cavity. Pyr, per se, can improve the metabolic pathway of carbohydrate and has strong anti-oxidative capacity. Lactate and bicarbonate, however, do not have these features, and even have toxicity (Acta Pharmacol Sin 22:385-92, 2001; Artif Organs 29:976-80, 2005; Am J Nephrol 25:55-63, 2005). Thus, Pyruvate-based Peritoneal Dialysis Solution (P-PDS) or hemofiltration substitute solution is not only a dialysis solution, in which Pyr only acts as a buffer but also a therapeutic agent for treatment and protection of general organ function of dialysis patients.

(1) Pyruvate-Based Peritoneal Dialysis Solution (P-PDS):

The invention provides double-chambered bag, wherein the smaller one contains stable pure NaPyr solution (250-400 mM), pH 4.0-5.0, preferably pH 4.5. The bigger one contains a mixed solution of 0-15 mM NaLac, and the corresponding concentrations of glucose and other conventional chemical ingredients, pH 5.0-5.5 after mixing with NaPyr solution. The smaller one contains a mixed solution of the same dosage of NaPyr and 50% glucose, pH 3.0-3.5. pH of the solution of the other ingredients in the bigger one is 7.0-7.5.

In another preferred embodiment of the invention, the smaller one only contains 50% glucose, pH 3.0. The bigger one contains a mixed solution of 0-15 mM NaLac, 25-40 mM NaPyr and the corresponding concentrations of other conventional chemical ingredients, pH 5.0-5.5 after mixing with 50% glucose.

In another preferred embodiment of the invention, it provides one-chambered bag of conventional peritoneal dialysis solution, in which NaLac is partly or wholly replaced by 25-40 mM NaPyr, with other ingredients and pH value unchanged.

(2) Pyruvate-Based Hemofiltration (HF) Substitute Solution:

The invention also provides double-chambered bag or one-chambered bag as described above to form hemofiltration (HF) solution containing NaPyr correspondingly. But as compared to P-PDS, the concentration of glucose contained in HF substitute solution is less than 1% to 1.5% (<1-1.5%), the concentration of NaPyr is ≤30-40 mM, and the concentrations of KCl and CaCl$_2$ are lower, pH 5.0-7.0. It is 4,000-5,000 ml per bag.

Pyruvate-based Hemofiltration (HF) substitute solution can be used for regular dialysis patients with kidney failure and the intensive cared patients.

As compared to the traditional NaLac-based HF solution, the Pyruvate-based HF solution has the following advantages:

1, Due to better buffering capacity than lactate, it can effectively correct and maintain the acid-base equilibrium of the patients treated by hemofiltration;

2, It is specifically indicative for hyperlactacidemia and lactic acidosis;

3, Due to the large amount of Pyr introduced, it can protect and cure dysfunction of organs.

(3) Pyruvate-Based Hemodialysis (HD) Solution:

As for the regular alkaline concentrated solution (B concentrated solution) prepared temporarily by NaHCO$_3$ and NaCl powder, NaHCO$_3$ powder can be replaced partly by NaPyr powder to be used for regular hemodialysis treatment within 12 hours from preparing.

The aqueous solution containing sodium pyruvate for medical use provided by the invention can also be used in food industry and cosmetic industry. The said solution contains the following components:

(a) 10-1,200 mM sodium pyruvate;
(b) a stabilizer of sodium pyruvate, which is selected from:
(b1) hydrogen ion, which makes the solution at pH of 3.5-6.0; and/or
(b2) NaCl, which provides additional Na$^+$ of at least 20 mM; and
(c) pharmaceutically accepted water for solvents, and after the solution is stood for 6 months under 25° C., the content of sodium pyruvate in the solution satisfies the following equation:

$$\frac{C_{the\ sixth\ month}}{C_{zero\ time}} \times 100\% \geq 95\%$$

wherein, $C_{the\ sixth\ month}$ means the concentration of sodium pyruvate in the solution after 6 months, $C_{zero\ time}$ means the initial concentration of sodium pyruvate in the solution of zero time.

The main advantages of the invention include:

1, providing a stable solution of NaPyr.

2, producing various solutions comprised of stable NaPyr being widely used in:

a. shock-resuscitation and intravenous fluid therapy;

b. correction of severe metabolic acidosis and treatment of dysfunction of important organs. As a novel buffer, which is not only a volume expander, but also is a therapeutic agent for acidosis correction and organ function;

c. kidney failure replacement therapy.

3, not only offering the effect of passive dialysis as a dialysis solution, but also using as active therapeutic agent for kidney failure and its complications.

4, being readily available of the raw material with low cost.

The invention is further illustrated by the following examples. It should be appreciated that these examples are only intended to illustrate the invention, but not to limit the scope of the invention. The particular conditions of the experimental methods are not disclosed in the following examples, and these methods are performed under routine conditions, or as instructed by the manufacturers. All parts, percents, ratios are calculated based on weight, unless otherwise specified.

Unless otherwise defined, all the technical and scientific terms as used herein have the same meaning as known by the skills in the art. Additionally, any method or material similar or equivalent to the contents described herein can be applied to the methods of the invention. The preferred methods and materials as described herein are only illustrative.

HPLC Assay for the content of sodium pyruvate:

Chromatographic column: Phenomenex 250×4.6 mm, 4.0 μm, column temperature: room temperature;

Stationary phase: Synergi Fusion-RP-80R;

Mobile phase: 0.025% trifluoroacetate (TFA);

Flow rate: 10.0 ml/min;

Sample volume: 20 μl;

Retention time of pyruvic acid or its salts: 4.1-4.6 min (4.33 min);

UV 210 nm.

HPLC Assay for the content of dimer:

Chromatographic column: Phenomenex 250×4.6 mm, 4.0 μm, column temperature: room temperature;

Stationary phase: Synergi Fusion-RP-80R;

Mobile phase: 0.025% trifluoroacetate (TFA);

Flow rate: 1.0 ml/min;

Sample volume: 20 μl;

Retention time of dimer: 4.8-6.1 min (5.48 min);

UV 210 nm.

EXAMPLE 1

Preparation of Aqueous Solution of Pure NaPyr 110.0 g NaPyr was dissolved in pure water for medical injection and the water for injection was added to 1000 ml, i.e.

110.0 g NaPyr per 1,000 ml solution. The reaction was agitated to dissolve the solid completely, the concentration of which was 11.0%, i.e. 1,000 mM. The pH value was adjusted to 4.5 by 0.1 M HCl.

EXAMPLE 2

The Stability of Aqueous Solution of Pure NaPyr

The aqueous solution of pure NaPyr prepared in Example 1 was stood for 6 months under sterilized condition and 25° C. Then the concentrations of NaPyr and dimer in the solution were determined.

The result was that the concentration of NaPyr was >98%, and the concentration of detectable dimer was <2.0%.

The result showed that the stability of the aqueous solution of pure NaPyr is kept for at least 6 months at room temperature, as determined by HPLC.

EXAMPLE 3

Preparation of Hyperosmotic Aqueous Solution of NaCl/NaPyr

Both 71.5 g NaPyr and 38.0 g NaCl were dissolved in pure water for medical injection, and the reaction was agitated to dissolve the solid completely. The water for injection was added to 1,000 ml, i.e. 7.15% NaPyr and 3.80% NaCl. The pH value was adjusted to 4.5 by small amount of 0.1 M HCl. Both the $Na^+$ concentration and the osmotic pressure of the solution were equivalent to those of 7.5% hyperosmotic NaCl. The theoretical value of osmotic pressure of the solution was 2,600 mOsm/L.

EXAMPLE 4

The Stability of Hyperosmotic Aqueous Solution of NaCl/NaPyr

The hyperosmotic aqueous solution of NaCl/NaPyr prepared in Example 3 was stood for 6 months under the sterilized condition and 25° C. Then the concentrations of NaPyr and dimer in the solution were determined.

The result showed that the solution is as stable as the solution prepared in Example 1. The concentration of NaPyr was >98%, and the concentration of detectable dimer was <2.0%.

EXAMPLE 5

Preparation of Compound Normal Saline

Both 5.5 g NaPyr and 6.08 g NaCl were dissolved in pure water for medical injection, the reaction was agitated to dissolve the solid completely. The water for injection was added to 1,000 ml, i.e. 0.61% NaCl and 0.55% NaPyr. In which the concentration of $Na^+$ was 154 mM (equivalent to 0.9% NaCl), that of $Cl^-$ was 104 mM, that of Pyr was 50 mM. The pH value was adjusted to 4.5 by small amount of 0.1 M HCl.

EXAMPLE 6

The Stability of Compound Normal Saline

The compound normal saline prepared in Example 5 was stood for 6 months under the sterilized condition and 25° C. Then the concentrations of NaPyr and dimer in the solution were determined.

The result showed that the solution is as stable as the solution prepared in Example 1. The concentration of NaPyr was >98%, and the concentration of detectable dimer was <2.0%.

EXAMPLE 7

Preparation of Modified Electrolyte Solution of NaPyr 3.08 g NaPyr, 6.55 g NaCl, 0.224 g KCl, 4.416 g $CaCl_2.2H_2O$, and 0.061 g $MgCl_2.6H_2O$ were dissolved in pure water for medical injection, the reaction was agitated to dissolve the solid completely. The water for injection was added to 1,000 ml, i.e. the concentrations (mM) were: $Pyr^-$ 28; $Na^+$ 140; $Cl^-$ 119; $K^+$ 3.0; $Ca^{2+}$ 3.0; and $Mg^{2+}$ 0.3. The pH value was adjusted to 4.5 by 0.1 M HCl.

EXAMPLE 8

The Stability of Modified Electrolyte Solution of NaPyr

The modified electrolyte solution of NaPyr prepared in Example 7 was stood for 6 months under the sterilized condition and 25° C. Then the concentrations of NaPyr and dimer in the solution were determined.

The result showed that the solution is as stable as the solution prepared in Example 1. The concentration of NaPyr was >98%, and the concentration of detectable dimer was <2.0%.

EXAMPLE 9

Preparation of Peritoneal Dialysis Solution I 30 g glucose, 8.8 g NaPyr, 11.817 g NaCl, 1.03 g $CaCl_2.2H_2O$, and 0.304 g $MgCl_2.6H_2O$ were dissolved in pure water for medical injection, the reaction was agitated to dissolve the solid completely. The water for injection was added to 2 L, which meant the concentrations of the chemicals were: 1.5% glucose, 40 mM NaPyr, 101 mM NaCl, 3.5 mM $CaCl_2.2H_2O$, and 0.75 mM $MgCl_2.6H_2O$. The pH value was adjusted to 5.0 by small amount of 0.1 M HCl.

EXAMPLE 10

Preparation of Peritoneal Dialysis Solution II 60 ml of 50% glucose (pH 3.0-3.5) was placed in a smaller chamber to be the solution in the smaller chamber. 8.8 g NaPyr, 11.817 g NaCl, 1.03 g $CaCl_2.2H_2O$, and 0.304 g $MgCl_2.6H_2O$ were dissolved in pure water for medical injection, the reaction was agitated to dissolve the solid completely. The water for injection was added to 1940 mL, and the pH value was adjusted to 6.0 by small amount of 0.1 M HCl, which formed the solution in bigger-chamber. After mixing the solutions in the two chambers evenly, the concentrations were: 1.5% glucose, 40 mM NaPyr, 101 mM NaCl, 3.5 mM $CaCl_2.2H_2O$, and 0.75 mM $MgCl_2.6H_2O$, pH 5.5.

EXAMPLE 11

Preparation of Peritoneal Dialysis Solution III 200 ml of 400 mM or 100 ml of 800 mM aqueous solution of pure NaPyr prepared as Example 1 was placed in smaller-chamber to be the solution in the smaller-chamber, pH 4.5. 30 g glucose, 11.817 g NaCl, 1.03 g $CaCl_2.2H_2O$, and 0.304 g $MgCl_2.6H_2O$ were dissolved in pure water for medical injection, the reaction was agitated to dissolve the solid completely. The water for medical injection was added to 1,800 ml or 1,900 ml, and the pH value was adjusted to 5.5-6.5 by 0.1 M HCl, which formed the solution of bigger-chamber. Or glucose and NaPyr were dissolved together in the smaller-chamber to be the solution in the smaller-chamber, pH 3.0-4.5, with the other ingredients dissolved in the bigger-chamber to be the solution in bigger-chamber, pH 7.0-7.5. After mixing the solutions in the two chambers evenly, the concentrations of the chemicals were: 1.5% glucose, 40 mM NaPyr, 101 mM NaCl, 3.5 mM $CaCl_2.2H_2O$, and 0.75 mM $MgCl_2.6H_2O$, pH 5.0-5.5 or pH 6.5-7.0, respectively.

EXAMPLE 12

The Stability of Peritoneal Dialysis Solution I

The solution prepared in Example 9 was stood for 6 months under the sterilized condition and 25° C. Then the concentrations of NaPyr and dimer in the solution were determined.

The result showed that the solution was as stable as the solution prepared in Example 1.

EXAMPLE 13

The Stability of Peritoneal Dialysis Solution II

The solution in the bigger-chamber prepared in Example 10 was stood for 6 months under the sterilized condition and 25° C. Then the concentrations of NaPyr and dimer in the solution were determined.

The result showed that the solution was as stable as the solution prepared in Example 1.

EXAMPLE 14

The Stability of Peritoneal Dialysis Solution III

The solution in the smaller-chamber prepared in Example 11 was stood for 6 months under the sterilized condition and 25° C. Then the concentrations of NaPyr and dimer in the solution were determined.

The result showed that the solution was as stable as the solution prepared in Example 1.

EXAMPLE 15

Preparation of Hemofiltration (HF) Substitute Solution 1,350 ml of the aqueous solution of pure NaPyr prepared in Example 1 (1,000 mM, pH 4.5) was placed in smaller-chamber to be the solution in the smaller-chamber. 60 g glucose, 23.693 g NaCl, 0.596 g KCl, 1.104 g $CaCl_2.2H_2O$, and 0.608 g $MgCl_2.6H_2O$ were dissolved in pure water for medical injection to a volume of 2,650 ml, and the pH value was adjusted to 6.5 by small amount of 0.1 M HCl, the reaction was agitated to dissolve the solid completely, and formed the solution in the big-chamber. After mixing the solutions in the two chambers evenly, the concentration of the chemicals are: 33.75 mM NaPyr, the concentrations of other ingredients were conventional, pH 6.0.

EXAMPLE 16

The Stability of Hemofiltration (HF) Substitute Solution

The solution in the smaller-chamber prepared in Example 15 was stood for 6 months under the sterilized condition and 25° C. Then the concentrations of NaPyr and dimer in the solution were determined.

The result showed that the solution was as stable as the solution prepared in Example 1.

Owing to the clinical benefits of NaPyr and its inherent instability, a lot of newly commercialized aqueous solutions containing NaPyr will be produced according to the invention. These solutions will be used widely in clinical practices and treatment, far beyond the above mentioned examples. For example, stable aqueous solutions containing NaPyr can be used for treating intracranial hypertension, cerebral edema, and severe hypoglycemia, etc. Alternatively, the aqueous solutions of Pyr can be used for improving various artificial oxygen carriers, such as HBOC-201, i.e. Hemopure: an artificial oxygen carriers containing bovine hemoglobin dissolved in lactate equilibrium solution, i.e. the NaLac or part of NaCl in the solution is replaced by stable aqueous solution of NaPyr. Stable aqueous solutions of NaPyr also include organ preservative solution, cardioplegia solution, cardiopulmonary bypass surgery priming solution, hemocyte rejuvenation solution, and skin health solution, etc. Any other aqueous solutions containing stable NaPyr are based on the present invention, no matter it is prepared by the inventor or others.

All examples mentioned above are preferred ones of the invention, which are not intended to limit the scope of the substantial technical contents of the invention. The substantial technical contents of the invention are defined broadly in the scope of the claims. If the technical entities or methods accomplished by others are completely the same as those defined in the scope of the claims, or their equivalent modifications, they will fall within the scope of the invention defined by the appended claims of the application.

What is claimed is:

1. A stabilized sodium pyruvate aqueous solution for infusion into a subject, comprising:
   (a) 10-1,200 mM sodium pyruvate;
   (b) a stabilizer of sodium pyruvate;
   (c) hydrochloric acid; and
   (d) pharmaceutically accepted water for solvents,
   wherein the stabilizer of sodium pyruvate includes hydrogen ion derived from the hydrochloric acid,
   wherein the hydrogen ion derived from the hydrochloric acid is present in an amount sufficient to (1) attain a pH of 3.0 or more and less than 5.0 in the solution; and (2) stabilize the sodium pyruvate in the solution so that after the solution is stored for 6 months under 25° C., the content of sodium pyruvate in the solution satisfies the following equation:

$$\frac{C_{the\ sixth\ month}}{C_{zero\ time}} \times 100\% \geq 95\%$$

wherein $C_{the\ sixth\ month}$ means the concentration of sodium pyruvate in the solution after 6 months of storage of the solution and $C_{zero\ time}$ means the initial concentration of sodium pyruvate in the solution before the storage of the solution, and wherein the hydrogen ion derived from the hydrochloric acid is present in an amount sufficient to stabilize the sodium pyruvate in the solution so that after the solution is stored for 6 months under 25° C., a molar ratio between a dimer of sodium pyruvate present in the solution after being stored under 25° C. for 6 months and sodium pyruvate before the storage of the solution is less than 1:20.

2. The aqueous solution of claim 1, wherein the aqueous solution contains 50-1,000 mM sodium pyruvate.

3. The aqueous solution of claim 1 wherein the aqueous solution is a hyperosmotic solution which contains 100-1,000 mM sodium pyruvate, 200-800 mM NaCl, and hydrogen ion in an amount sufficient to attain a pH of 4.0 or above and less than 5.0 in the solution, and the osmotic pressure of which is 2,000-3,000 mOsm/L.

4. The aqueous solution of claim 1 wherein the aqueous solution is a compound normal saline, which contains 80-20 mM sodium pyruvate, 80-130 mM NaCl, and hydrogen ion in an amount sufficient to attain a pH of 4.0 or above and less than 5.0 in the solution, and the osmotic pressure of which is 280-320 mOsm/L.

5. The aqueous solution of claim 1 wherein the aqueous solution contains 10-80 mM $Pyr^-$, 120-150 mM $Na^+$, 90-130 mM $Cl^-$, 1-4 mM $K^+$, 1-5.0 mM $Ca^{2+}$, and 0.1-1.0 mM $Mg^{2+}$.

6. A kit which comprises:
(i) container 1, which contains solution 1, wherein the solution 1 is the aqueous solution of claim 1, and
(ii) container 2, which contains solution 2, wherein the solution 2 is mixed with solution 1 before use.

7. The kit of claim 6 wherein the solution 2 is selected from the group consisting of:
100-800 mM NaCl solution, and/or 0-25 mM sodium lactate, and 1.0-10.0% glucose or colloidal additives.

8. The aqueous solution of claim 1, wherein the stabilizer of sodium pyruvate further comprises NaCl, wherein the NaCl is present in an amount sufficient to provide at least 20 mM $Na^+$ in addition to an amount of $Na^+$ from the sodium pyruvate.

9. A method for preparing a stabilized sodium pyruvate aqueous solution in accordance with claim 1, comprising:
a) dissolving an amount of sodium pyruvate in pharmaceutically accepted water for solvents to form a mixture, wherein the amount of sodium pyruvate dissolved is such that the mixture includes 10-1,200 mM sodium pyruvate;
b) adding a stabilizer of sodium pyruvate to the mixture obtained in (a) to form the stabilized aqueous solution of sodium pyruvate in accordance with claim 1.

10. A method for preparing the aqueous solution of claim 9, further comprising dissolving NaCl in the mixture obtained in (a), wherein NaCl is added in an amount sufficient provide at least 20 mM $Na^+$ in addition to an amount of $Na^+$ from the sodium pyruvate.

* * * * *